United States Patent [19]

Ishizuka et al.

[11] Patent Number: 4,511,564
[45] Date of Patent: Apr. 16, 1985

[54] METHODS OF CONTROLLING THE CONCENTRATION OF CALCIUM IN THE SERUM OF WARM-BLOODED ANIMALS AND PHARMACEUTICAL COMPOSITIONS TO BE USED THEREFOR

[75] Inventors: Seiichi Ishizuka, Hino; Junji Kubo, Kanagawa, both of Japan

[73] Assignee: Teijin Limited, Osaka, Japan

[21] Appl. No.: 454,309

[22] Filed: Dec. 29, 1982

[30] Foreign Application Priority Data

Dec. 29, 1981 [JP] Japan .................. 56-213108
Dec. 29, 1981 [JP] Japan .................. 56-213109
Oct. 7, 1982 [JP] Japan .................. 57-175265

[51] Int. Cl.$^3$ ............................................ A61K 31/59
[52] U.S. Cl. .................................................. 514/167
[58] Field of Search ...................... 424/236; 260/397.2

[56] References Cited

U.S. PATENT DOCUMENTS 4,307,231 7/1980 DeLuca et al. ............... 260/397.2
4,336,193 6/1982 DeLuca et al. ............... 260/397.2

OTHER PUBLICATIONS

Tanaka et al., Proc. Natl. Acad. Sci., vol. 77, No. 11, pp. 6411–6414, (1980), "Role of Kidney Tissue in the Production of 25-Hydroxyvit-D$_3$-26,23-Lactone and 1α,25-dihydroxyvitamin D$_3$-26,23-Lactone".
FEBS Lett. (1982) 139(2), pp. 267–270, as shown in Chem. Abstract vol. 96(23), Par. 198, 337(p).

Primary Examiner—Elbert L. Roberts
Attorney, Agent, or Firm—Sughrue, Mion, Zinn, Macpeak, and Seas

[57] ABSTRACT

The present invention relates to a method of controlling the concentration of calcium in the serum of warm-blooded animals characterized by the administration of a pharmaceutically effective amount of 25-hydroxyvitamin D$_3$-26,23-lactones expressed by the following formula (I)

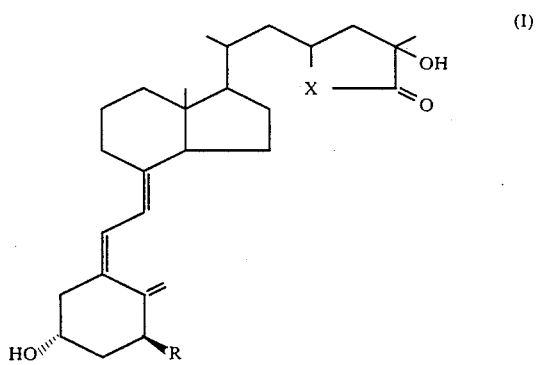

(I)

wherein R indicates a hydrogen atom or a hydroxyl group and X indicates —O— or —O—O—, to warm-blooded animals, and a pharmaceutical composition to be used for controlling the concentration of calcium in the serum of warm-blooded animals which comprises 25-hydroxyvitamin D$_3$-26,23-lactones expressed by the above-mentioned formula (I) and a pharmaceutically acceptable carrier.

25-hydroxyvitamin D$_3$-26,23-lactones are desirably used especially for the treatment or prevention of the diseases resulting from the high calcium levels in the serum.

7 Claims, 6 Drawing Figures

● : 25-OH-D$_3$-26,23-LACTONE
○ : 1α,25-(OH)$_2$D$_3$
□ : CONTROL
△ : 25-OH-D$_3$

METHODS OF CONTROLLING THE CONCENTRATION OF CALCIUM IN THE SERUM OF WARM-BLOODED ANIMALS AND PHARMACEUTICAL COMPOSITIONS TO BE USED THEREFOR

BACKGROUND OF THE INVENTION

1. Field of the Invention

The present invention relates to a method of controlling the concentration of calcium in the serum of warm-blooded animals. More particularly, the invention is concerned with a method of controlling the calcium level in the serum of warm-blooded animals by administering 25-hydroxyvitamin $D_3$-26,23-lactones to them and a pharmaceutical composition comprising 25-hydroxyvitamin $D_3$-26,23-lactones for controlling the concentration of calcium in the serum of a warm-blooded animal and a pharmaceutically acceptable carrier.

2. Description of the Prior Art $1\alpha,25$-dihydroxycholecalciferol, $1\alpha$-hydroxycholecalciferol, $1\alpha,24$-dihydroxycholecalciferol, and the like, for instance, have hitherto been known as useful compounds for the treatment of osteoporosis, osteomalacia, etc. However, these compounds incur possibility of causing ill effects such as hyper-calsemia etc., when administered in large doses.

Calcitonin is known as a drug for the treatment of hypercalsemia, etc., but it has a demerit of being not administrable orally.

Meanwhile, $1\alpha,25$-dihydroxyvitamin $D_3$-26,23-lactone has recently been isolated from the serum of rats and chemically identified as a novel metabolite of $1\alpha$-hydroxyvitamin $D_3$ or $1\alpha,25$-dihydroxyvitamin $D_3$ (Arch. Biochem. Biophs. 204, pp. 387–391, 1980; FEBS LETTERS, 134, pp. 207–211, 1981).

Also 25-hydroxyvitamin $D_3$-26,23-lactone was isolated from the serum of chickens, rats or pigs and identified as such (Biochemistry, 18, pp. 4775–4780, 1979; Biochemical and Biophysical Research Communication, 89, pp. 286–293, 1979; Biochemical and Biophysical Research Communication, 93, pp. 149–154, 1980).

In reference to reports on the biological activity of said 25-hydroxyvitamin $D_3$-26,23-lactone, International Publication Number WO 81/500045 discloses that rats which had been fed with a vitamin $D_3$ deficient diet were given 25-hydroxy-vitamin $D_3$-26,23-lactone. The measurement of concentration of calcium contained in the serum made 12 hours after the administration showed that 25-hydroxyvitamin $D_3$-26,23-lactone increased the concentration of calcium in the serum and that accordingly "it has the activity similar to vitamin D in promoting the bone calcium mobilization."

With regard to $1\alpha,25$-dihydroxyvitamin $D_3$-26,23-lactone, no literature has yet been published to report on its biological activity based on the concrete pharmacological data.

SUMMARY OF THE INVENTION

After a close and patient study made on the biological activity of 25-hydroxyvitamin $D_3$-26,23-lactone, the inventors have found that, when 25-hydroxyvitamin $D_3$-26,23-lactone is given to vitamin $D_3$ deficient rats and the concentration of calcium in the serum is measured 48 to 96 hours after its administration, the calcium level in the serum is remarkably low beyond expectations.

Also it has been made clear that $1\alpha,25$-dihydroxyvitamin $D_3$-26,23-lactone decreases the calcium level likewise. Furthermore, the inventors have isolated and identified 25-hydroxyvitamin $D_3$-26,23-peroxylactone as a novel metabolite and found that this new compound decreases the calcium level in the serum in the same manner.

The present invention is achieved on the basis of these facts mentioned above. In more detail, the present invention has been completed on the finding that 25-hydroxyvitamin $D_3$-26,23-lactone and its derivatives decrease the calcium level in the serum, that these compounds can be administered orally, and that these compounds are useful for the treatment of hypercalcemia etc. arising from the administration of $1\alpha,25$-dihydroxycholecalciferol and the like.

The present invention is concerned with a method of controlling the concentration of calcium in the serum of warm-blooded animals characterized by the administration of a pharmaceutically effective amount of 25-hydroxyvitamin $D_3$-26,23-lactone or its derivatives expressed by the following formula (I)

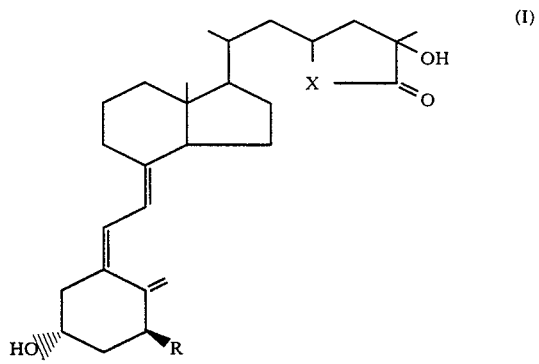

wherein R indicates a hydrogen atom or a hydroxyl group and X indicates —O— or —O—O—, to warm-blooded animals, and a pharmaceutical composition to be used for controlling the concentration of calcium in the serum which comprises 25-hydroyvitamin $D_3$-26,23-lactone or its derivatives expressed by the above-mentioned formula (I) and a pharmaceutically acceptable carrier.

Figure 1:
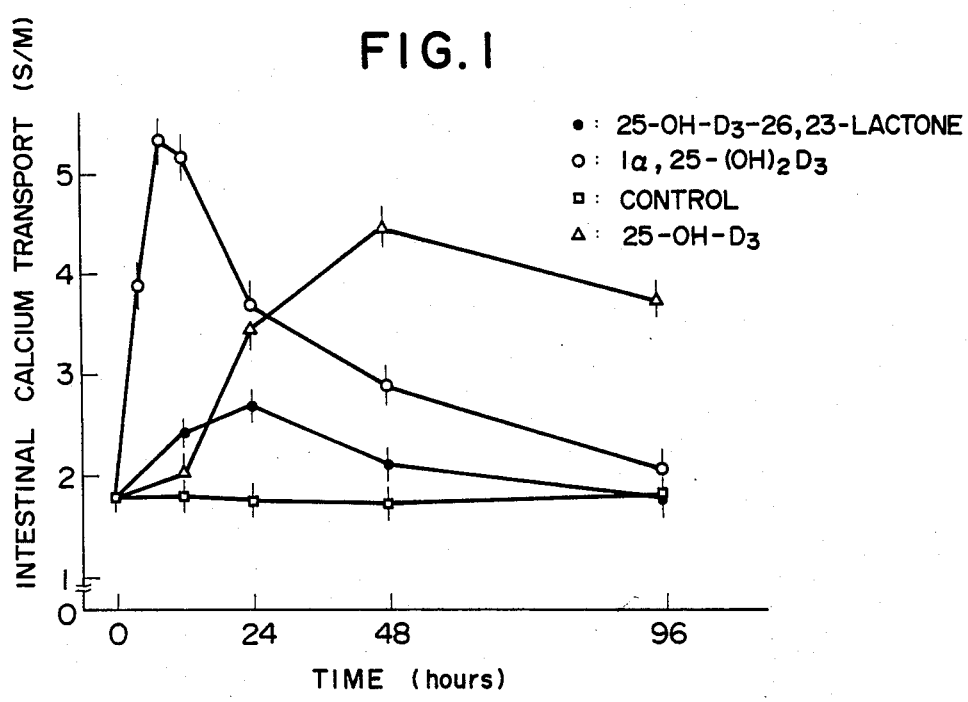
FIG. 1 shows the influence of 25-hydroxyvitamin $D_3$-26,23-lactone on the intestinal calcium transport

DESCRIPTION OF THE PREFERRED EMBODIMENTS 25-hydroxyvitamin $D_3$-26,23-lactones to be used in this invention are expressed by the aforementioned formula (I), in which R indicates a hydrogen atom or a hydroxyl group and X indicates —O— or —O—O—.

25-hydroxyvitamin D3-26,23-lactones, in which X in said formula (I) is —O—, are expressed by the following formula (I)-1

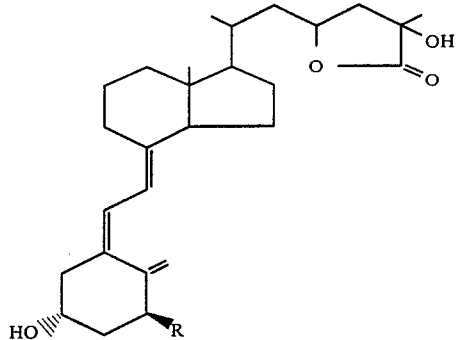

wherein R indicates a hydrogen atom or a hydroxyl group. As the compounds of this kind, 25-hydroxyvitamin D3-26,23-lactone and 1α,25-dihydroxyvitamin D3-26,23-lactone may be mentioned.

25-hydroxyvitamin D3-26,23-lactone is a known compound and is isolated from the serum of vitamin D3 repleted rats, chickens, pigs, etc. and identified as the resulting metabolite (FEBS LETTERS, 134, pp. 207–211, 1981; Biochemistry, 18, pp. 4775–4780, 1979; Biochemical and Biophysical Research Communication, 89, pp. 286–293, 1979).

This compound can also be obtained by means of chemical synthesis. There are some known methods, including, for instance, one in which it can be obtained by allowing aldehyde compound expressed by the following formula

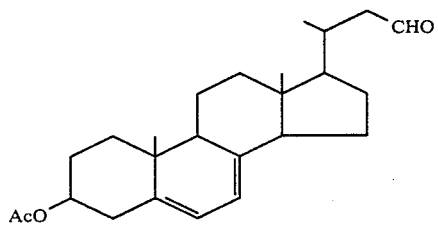

to react with acetone to make a corresponding β-hydroxyketone compound, followed by cyanohydrin synthesis (Tetrahedron Letters, 21, pp. 4667–4670, 1980) and one in which an aldehyde compound obtained from ergosterol is used as a material (Journal of Organic Chemistry, 46, pp 3422–3428, 1981).

25-hydroxyvitamin D3-26,23-lactone has an asymmetric carbon atom at its 25-position and 23-position and in the present invention, the 25-position and the 23-position may be either R-configuration or S-configuration or a mixture consisting of R-configuration and S-configuration mixed at an optional ratio. Of all such compounds, natural type, 23(S),25(R)-25-hydroxyvitamin D3-26,23-lactone is particularly appropriate for the object in the present invention because of its desirable physiological functions.

1α,25-dihydroxyvitamin D3-26,23-lactone is a publicly known compound and is isolated from the serum of rats or dogs as a metabolite of administered 1α-hydroxyvitamin D3 or 1α,25-dihydroxyvitamin D3 (Arch. Biochem. Biophs., 204, pp. 387–391, 1980).

1α,25-dihydroxyvitamin D3-26,23-lactone can also be obtained by incubating 25-dydroxyvitamin D3-26,23-lactone with a homogenate of the kidney of chick (FEBS LETTERS, 134, pp. 207–211, 1981).

Chemical synthesis can also offer 1α,25-dihydroxyvitamin D3-26,23-lactone. It can be obtained synthetically from a material compound of ergosterol derivative having a hydroxyl group at the 1α-position as shown in the following formula

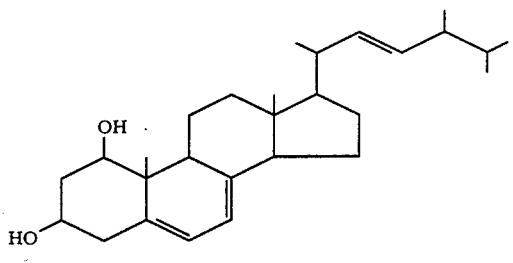

according to the method described in the Journal of Organic Chemistry, 46, pp. 3422–3428, 1981. It can also be synthesized with the use of aldehyde compound expressed by the folloing formula as a material compound

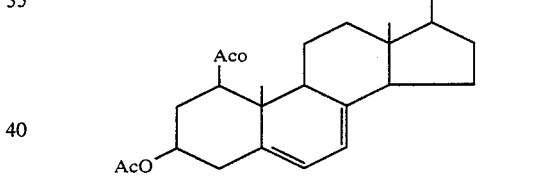

according to the synthetic method described in the Tetrahedrom Letters, 21, pp. 4667–4670, 1980.

Furthermore, it can be synthetically obtained by directly subjecting 25-hydroxyvitamin D3-26,23-lactone to 1α-hydroxylation method according to the method shown in the Proc. Natl. Acad. Sci. U.S.A., vol. 75, No.5, pp. 2080–2081, 1978.

As in the case of 25-hydroxyvitamin D3-26,23-lactone, 1α,25-dihydroxyvitamin D3-26,23-lactone also has an asymmetric carbon atom at its 25-position and 23-position and in the present invention, the 25-position and 23-position may be either R-configuration or S-configuration or a mixture consisting of R-configuration and S-configuration mixed at an optional ratio. Of all these compound, a natural type, 23(S),25(R)-1α,25-dihydroxyvitamin D3-26,23-lactone is especially useful because of its desirable biological activity.

25-hydroxyvitamin D3-26,23-lactones, in which X in said formula (I) is —O—O—, are expressed by the following formula (I)-2

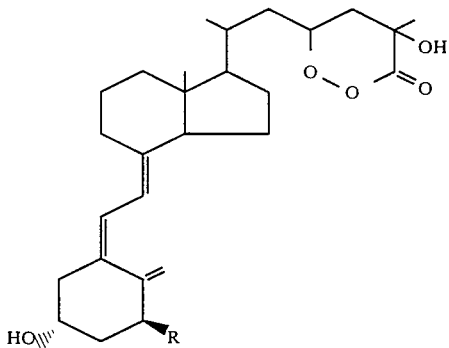

(I)-2 wherein R indicates a hydrogen atom or a hydroxyl group. As the compound of this kind, 25-hydroxyvitamin $D_3$-26,23-peroxylactone and $1\alpha$,25-hydroxyvitamin $D_3$-26,23-peroxylactone may be mentioned. These compounds are novel compounds first found by the present inventors and they are compounds which have a $\gamma$-peroxylactone structure on the side chain. 25-hydroxyvitamin $D_3$-26,23-peroxylactone can be obtained according to the following procedures: by first giving vitamin $D_3$ or 25-hydroxyvitamin $D_3$ to rats, chickens, pigs, etc. in a toxicologically permissible dose after the ordinary method such as oral administration, intravenous injection, and intramuscular injection, and then extracting the desired compound from the serum collected from the blood of the rats, chickens, pigs, etc. about 3 to 10 days after the administration as a metabolite of the administered vitamin $D_3$ or 25-hydroxyvitamin $D_3$, and finally isolating on Sephadex LH-20 column chromatography or high pressure liquid chromatography.

$1\alpha$,25-dihydroxyvitamin $D_3$-26,23-peroxylactone can be obtained as a metabolite of $1\alpha$-hydroxyvitamin $D_3$ or $1\alpha$,25-dihydroxyvitamin $D_3$ according to the same method as the isolation and extraction of 25-hydroxyvitamin $D_3$-26,23-lactone.

Of these 25-hydroxyvitamin $D_3$-26,23-lactones, 25-hydroxyvitamin $D_3$-26,23-lactone and $1\alpha$,25-dihydroxyvitamin $D_3$-26,23-lactone are desirable from the viewpoint of pharmacological founctions and chemical stability, of which $1\alpha$,25-dihydroxyvitamin $D_3$-26,23-lactone is especially desirable. Of $1\alpha$,25-dihydroxyvitamin $D_3$-26,23-lactone, 23(S), 25(R)-$1\alpha$,25-dihydroxyvitamin $D_3$-26,23-lactone, whose configuration around the carbon atoms at the 23- and 25-positions is the same as the natural type, is particularly desirable.

The aforementioned 25-hydroxyvitamin $D_3$-26,23-lactone and its derivatives have a function to control the calcium concentration in the serum of warm-blooded animals, especially a function to decrease the concentration of calcium in the serum of warm-blooded animals. Also 25-hydroxyvitamin $D_3$-26,23-lactone and its derivatives, of the present invention ensure high toxicological safety since it is a metabolite obtained in vivo from warm-blooded animals. Therefore, the present invention can be desirably applied to the treatment of diseases arising from the abnormally high concentration of calcium in the serum of warm-blooded animals. Also, in the case where a possible abnormal increase of calcium level in the serum of warm-blooded animals is foreseen, this invention can be used with the object of prevention before such abnormality takes place.

The present invention is appropriately applied to the treatment of diseases resulting from the high calcium levels in the serum, including, for instance, hypercalcemia due to the administration of $1\alpha$-hydroxyvitamin $D_3$, $1\alpha$,25-dihydroxyvitamin $D_3$, $1\alpha$,24-dihydroxyvitamin $D_3$, etc., hypercalcemia due to malignant tumor, hyperparathyroidism, and Behcet's disease etc.

The conditions to which the present invention is advisably applied include cases where vitamin D resistant patients who need the administration of vitamin $D_3$ in large doses and also patients with a malignant tumor who are afraid of having high calcium levels.

The present invention is originally designed to be fittingly applied to man; however, it also works usefully in the treatment of warm-blooded animals such as a pig, bovine, goat, sheep, horse, dog, cat, etc.

In the present invention, the aforementioned 25-hydroxyvitamin $D_3$-26,23-lactone and its derivatives are administered in a pharmaceutically effective amount such as 1 to 1000 ng/day/kg-body weight, desirably 5 to 200 ng/day/kg-body weight.

In the present invention, these 25-hydroxy-vitamin $D_3$-26,23-lactones can be administered once a day or several times, for instance, in two or three divided doses a day. The times of administration can be determined discretionarily in consideration of the conditions of diseased warm-blooded animals by a doctor in case of man and by a veterinarian or by a keeper under the direction of a veterinarian in case of warm-blooded animals other than man.

In the present invention, 25-hydroxyvitamin $D_3$-26,23-lactones can be administered to a living body via various routes. More particularly, 25-hydroxy-vitamin $D_3$-26,23-lactones can be administered either orally or parenterally, such as intramuscularly, intravenously, subcutaneously, or by way of a suppository, desirably orally. It is preferable to have these 25-hydroxyvitamin $D_3$-26,23-lactone and its derivatives administered in the form of a mixture combined with a pharmaceutically acceptable carrier. Thus the present invention offers a pharmaceutical composition for controlling the calcium concentration in the serum comprising 25-hydroxyvitamin $D_3$-26,23-lactone or its derivatives expressed by the aforementioned formula (I) and a pharmaceutically acceptable carrier. Since 25-hydroxyvitamin $D_3$-26,23-lactone and its derivatives have a specific pharmacological function to reduce the serum calcium levels, said pharmaceutical composition is very useful when used as a pharmaceutical composition to reduce the concentration of calcium in the serum.

As the pharmaceutically acceptable carrier, for instance, ethyl alcohol; such vegetable oils as corn oil, olive oil, cotton seed oil, coconut oil, almond oil, peanut oil, etc.; fish liver oil; oily esters such as Polysolvate 80 which is capable of making a pharmaceutical liquid composition; cacao butter, fatty acid triglyceride, etc. that are capable of making a pharmaceutical solid composition meltable at living body temperature; calcium carbonate, potato starch, alginic acid, lactose, etc. that are capable of making a pharmaceutical solid composition not meltable at living body temperature; and organic acid esters such as propylene glycol, polyethylene glycol, and ethyl oleate that make an aqueous or nonaqueous pharmaceutical solution or suspension composition may be mentioned.

The pharmaceutical composition of this invention may be made to contain such an antioxidant as ascorbic acid, butylated hydroxyanisole, and hydroquinone with the object of stabilizing 25-hydroxyvitamin $D_3$-26,23-lactones contained therein since it is unstable to oxidation, light, or heat. Also 25-hydroxyvitamin $D_3$-26,23-lactones may be contained in the pharmaceutical composition after it is made into a inclusion compound with the use of $\alpha$-, $\beta$-, or $\gamma$-cyclodextrin or methylated $\alpha$-, $\beta$-, or $\gamma$-cyclodextrin, for instance.

Furthermore, the present invention offers medicaments prepared in the form of a unit dose comprising a unit dose of 25-hydroxyvitamin $D_3$-26,23-lactone or its derivatives and a pharmacologically acceptable carrier for controlling the concentration of calcium in the serum.

As such medicaments, a tablet, pill, suger-coated tablet, powder, granule, hard or elestic gelatin capsule, buccal tablet, suppository, and injection, desirably a hard or elastic gelatin capsule, powder, and granule may be mentioned.

These medicaments are prepared as medicaments containing 0.05 to 10 µg, desirably 0.25 to 2 µg of 25-hydroxyvitamin $D_3$-26,23-lactones and are usually offered as orally administrative medicaments in the form of a hard or elastic gelatin capsule, powder, or granule, for instance.

Of 25-hydroxyvitamin $D_3$-26,23-lactone and its derivatives to be contained in a pharmaceutical composition or medicament in the form of a unit dose in the present invention, 25-hydroxyvitamin $D_3$-26,23-lactone and $1\alpha,25$-dihydroxyvitamin $D_3$-26,23-lactone are desirable, and of these two compounds $1\alpha,25$-dihydroxyvitamin $D_3$-26,23-lactone, especially 23(S),25(R)-$1\alpha,25$-dihydroxyvitamin $D_3$-26,23-lactone are desirable.

By way of illustration, but not by way of limitation, the following examples are given to illustrate the practice of this invention.

REFERENTIAL EXAMPLE 1

Preparation of 23(S),25(R)-25-hydroxyvitamin $D_3$-26,23-lactone

Male weanling rats of the Wistar strain were fed a normal vitamin $D_3$-containing diet (Nippon Clea Corp. CE-2: Ca, 1.0%; P, 1.0%; $D_3$, 2000 IU/kg) for 8 weeks ad libitum. The 150 rats were then dosed 2 times intramuscularly with $4 \times 10^5$ IU vitamin $D_3$ in 100 µl of ethanol at 3-day intervals. Three days after the second dose, the rats were anesthetized with ether and their blood was withdrawn from the abdominal aorta. The serum (600 ml) was diluted with the same volume of water and then extracted with 2 volumes of a chloroform/methanol (1:1) mixture. The chloroform extract of serum was chromatographed on a $1.5 \times 25$ cm Sephadex LH-20 column eluted with a chloroform/n-hexane (65:35) mixtue. The 24,25-$(OH:)_2D_3$ fraction from the Sephadex LH-20 column was then subjected to HPLC (high pressure liquid chromatography) on a Hitachi Model 635 equipped with a $4.6 \times 250$ mm Zorbax Sil column eluted with 9% isopropanol in n-hexane at a flow rate of 1 ml/min. 25-OH-$D_3$-26,23-lactone fraction was rechromatographed by using the same solvent. Thus obtained 23(S),25(R)-25-hydroxyvitamin $D_3$-26,23-lactone was further purified by HPLC using a Zorbax Sil column eluted with 1.5% methanol in dichloromethane at a flow rate of 1 ml/min.

REFERENTIAL EXAMPLE 2

Preparation of 23(S),25(R)-$1\alpha,25$-dihydroxyvitamin $D_3$-26,23-lactone

A male beagle dog (weighing 10 kg) was dosed orally with 2 mg of $1\alpha$-hydroxyvitamin $D_3$ dissolved in 20 ml of 0.2% Triton X-100 solution. Eight hours after the administration, the dog was anesthetized with Nembutal ® and the blood was withdrawn from the carotid artery. The serum (600 ml) obtained from the blood was diluted with the same volume of water and then extracted with 2 volumes of a chloroform:methanol (1:1) mixture. The obtained extract of serum was chromatographed on a $1.5 \times 25$ cm Sephadex LH-20 column eluted with a developing solvent of chloroform/n-hexane/methanol (75:23:2). The $1\alpha,24,25$-trihydroxyvitamin $D_3$ fraction from the Sephadex LH-20 column was then subjected to HPLC on a Zorbaxs Sil column eluted with 3.5% methanol in dichloromethane at a flow rate of 1 ml/mm. The $1\alpha,25$-dihydroxyvitamin $D_3$-26,23-lactone fraction from the HPLC was rechromatographed on HPLC under the same conditions. The obtained 23(S),25(R)-$1\alpha,25$-dihydroxyvitamin $D_3$-26,23-lactone was further purified by HPLC using a Zorbax Sil column eluted with 18% isopropanol in n-hexane at a flow rate of 1 ml/min.

REFERENTIAL EXAMPLE 3

Preparation of 25-hydroxyvitamin $D_3$-26,23-peroxylactone (i) Male weanling rats of the Wistar strain were fed a normal vitamin $D_3$-containing diet (Nippon Clea Corp. CE-2; Ca: 1.0%, P: 1.0%, vitamin $D_3$: 2000 IU/kg) for 8 weeks ad libitum. The 300 rats were then dosed intramuscularly with $4 \times 10^5$ IU of vitamin $D_3$ dissolved in 100 µl of ethanol, and after 3 days, they were again dosed intramuscularly with $4 \times 10^5$ IU of vitamin $D_3$ dissolved in 100 µl of ethanol. Three days after the second dose, the rats were anesthetized with ether and their blood was withdrawn from the abdominal aorta. The blood was immediately centrifuged and 1200 ml of serum was obtained. The serum (1200 ml) was diluted with the same colume of water and was then extrected with 2 volumes of chloroform/methanol (1:1) for 30 minutes. The chloroform phase was evaporated, and the residue was dried by ethanol azeotrope and used for chromatography. The chloroform extract of serum sample was chromatographed on a $1.5 \times 25$ cm Sephadex LH-20 column eluted with chloroform/n-hexane (65:35).

The 24,25-dihydroxyvitamin $D_3$ fractions from the column were separately pooled and concentrated. The 24,25-dihyroxyvitamin $D_3$ fraction was then subjected to high pressure liquid chromatography (HPLC) on a Hitachi Model 635 equpped with a $4.6 \times 250$ mm Zorbax Sil column eluted with 9% isopropanol in n-hexane at a flow rate of 1 ml/min. The eluate was continuously monitored by ultraviolet absorption at 264 nm, and the ultraviolet absorbing peaks were separately collected. The major ultraviolet absorbing peak eluted between 25-OH-$D_3$ and 24,25-$(OH)_2D_3$ had an ultraviolet absorption spectrum of the typical vitamin D cis-triene absorbance maximum at 264 nm and minimum at 228 nm. This fraction was chromatographed by HPLC using a $4.6 \times 250$ mm Zorbax Sil column eluted with 1.5% methanol in dichloromethane at a flow rate of 1 ml/min. The obtained 25-hydroxyvitamin $D_3$-26,23- peroxylactone was eluted immediately after the elution position of 25-OH-$D_3$. This metabolite was further purified by HPLC using a Zorbax Sil solumn eluted with 9% isopropanol in n-hexane at a flow rate of 1 ml/min. once more. It was eluted just before the elution position of 23(S),25(R)-25-OH-$D_3$-26,23-lactone or 24,25$(OH)_2D_3$.

(ii) The spectral data of thus obtained compounds are as follows:
 (a) UV spectrum:
  λ max: 264 nm
  λ min: 228 nm
 (b) Mass spectrum:
  (m/e); 412, 400, 372, 354, 339, 313, 271, 253, 136, 118
 (c) FD mass spectrum:
  Molecular ion peak: 444
 (d) Fourier transform infrared spectrum (FT-IR spectrum)
  A specific peak is detected at 1733 $cm^{-1}$ corresponding with the absorption of δ-lactone.

From the results mentioned above, it was confirmed that the obtained compound was 25-hydroxyvitamin $D_3$-26,23-peroxylactone.

EXAMPLE 1

Pharmacological functions of 25-hydroxyvitamin $D_3$-26,23-lactones (i) Influences of 25-hydroxyvitamin $D_3$-26,23-lactones on the intestinal calcium transport and the concentration of calcium in the serum (a) Male wealing rats of the Wistar strain were fed a vitamin $D_3$ deficient low calcium diet for 6 weeks ad libitum. After 6 weeks, the 5 rats, each weighing about 100 g, were dosed intravenously with 500 ng of 25-hydroxyvitamin $D_3$-26-23-lactone obtained in Referential Example 1, 250 ng of 1α,25-dihydroxyvitamin $D_3$, and 500 ng of 25-hydroxyvitamin $D_3$ dissolved respectively in 0.2 ml of 0.2% Triton X-100 solution. The rats were thereafter sacrificed, the intestinal calcium transport and the concentration of calcium in the serum were determined. The intestinal calcium transport was measured according to the method described by De Luca et al. (Am. J. Physiol., 216, pp. 1351–1359, 1969) and the concentration of calcium in the serum according to the OCPC method (Am. J. Clin. Pathol., 45, pp. 290–296, 1966).

Figure 2:
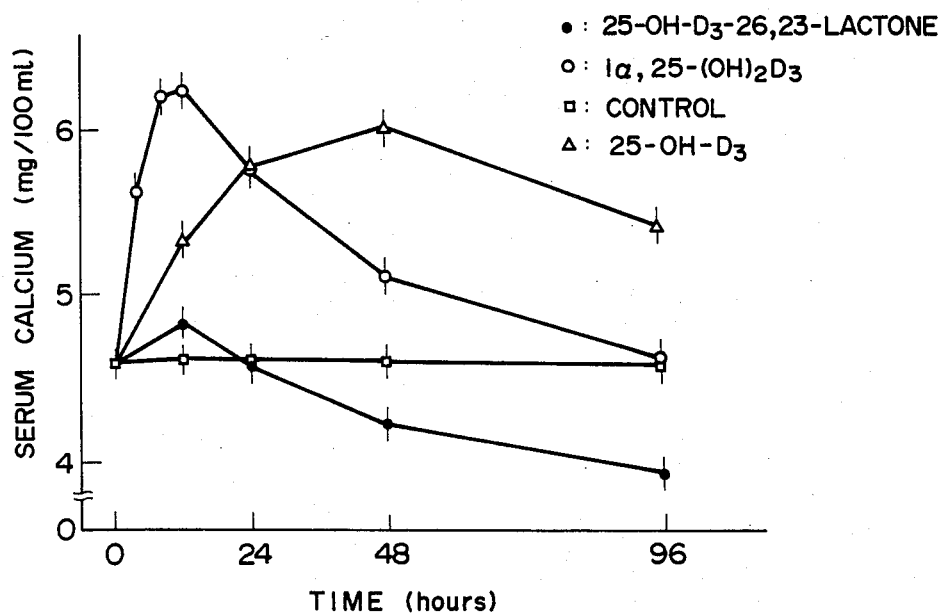
FIG. 2 shows the influence of 25-hydroxyvitamin $D_3$-26,23-lactone on the concentration of calcium in the serum.

The result of measurement of the intestinal calcium transport in shown in FIG. 1 and that of the concentration of calcium in the serum in FIG. 2.

(b) The same experiment as the preceding (a) was conducted with the use of 125 ng of 1α,25-dihydroxyvitamin $D_3$-25,23-lactone obtained in Referential Example 2 and 125 ng of 1α,25-dihydroxyvitamin $D_3$. The results are shown in FIG. 3 and FIG. 4.

(c) The same experiment as the foregoing (a) was conducted with the use of 125 ng of 25-hydroxyvitamin $D_3$-26,23-peroxylactone obtained in Referential Example 3 and 125 ng of 1α,25-dihydroxyvitamin $D_3$. The results are shown in FIG. 5 and FIG. 6.

Figure 3:
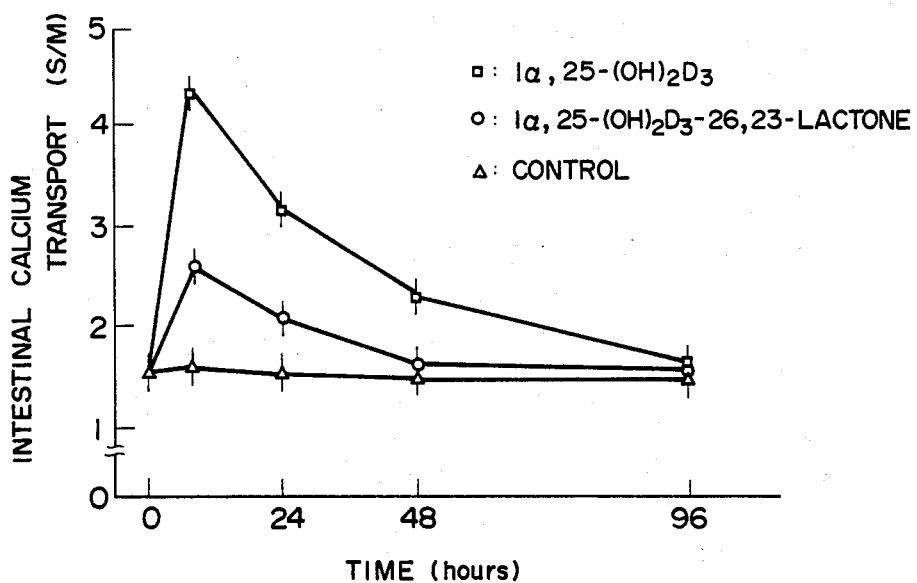
FIGS. 3 and 4 and FIGS. 5 and 6 respectively show the influences of $1\alpha,25$-dihydroxyvitamin $D_3$-26,23-lactone and 25-hydroxyvitamin $D_3$-26,23-peroxylactone on the intestinal calcium transport and the concentration of calcium in the serum.
Figure 5:
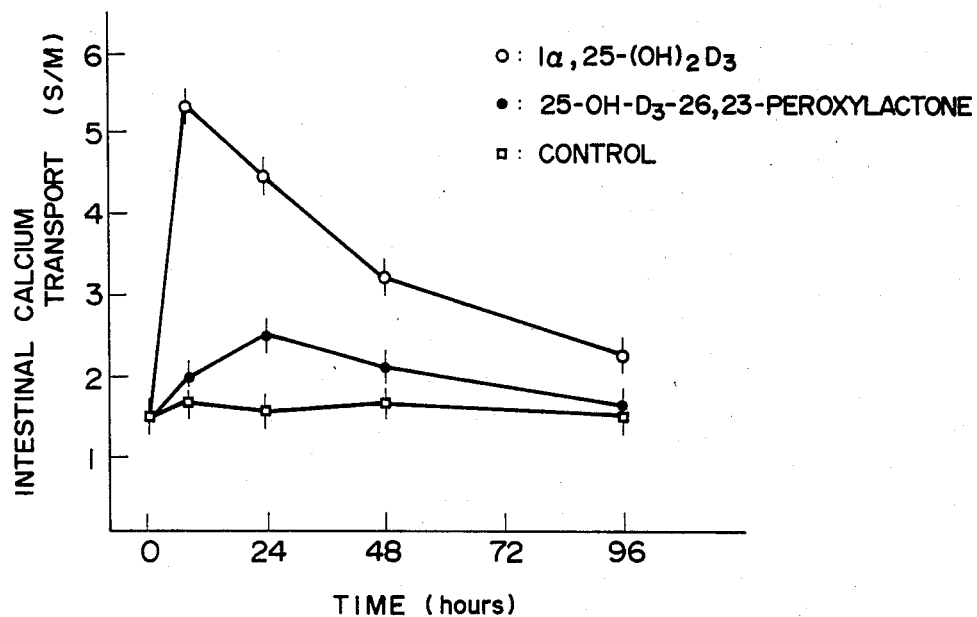

FIG. 1, FIG. 3, and FIG. 5 show that 25-hydroxyvitamin $D_3$-26,23-lactones of the present invention slightly stimulate the intestinal calcium transport.

Figure 4:
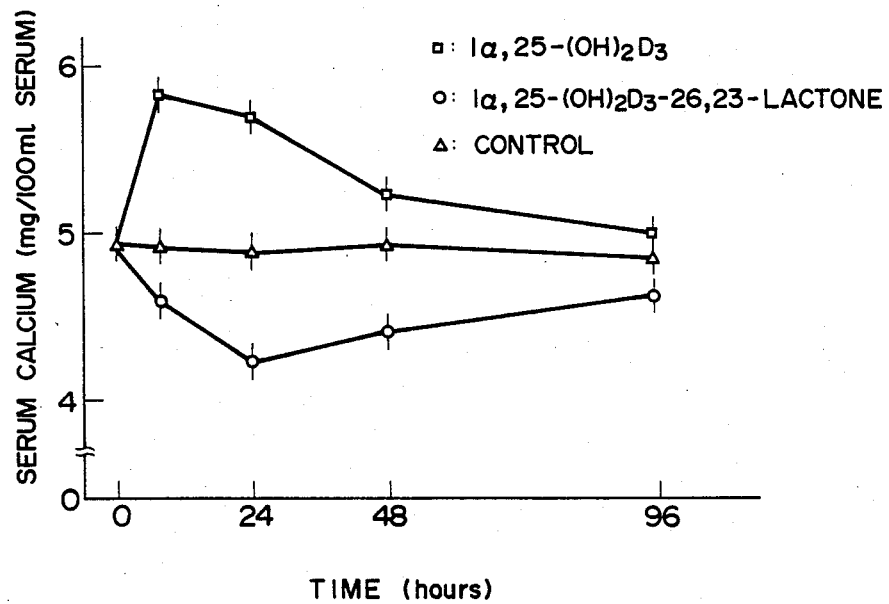
Figure 6:
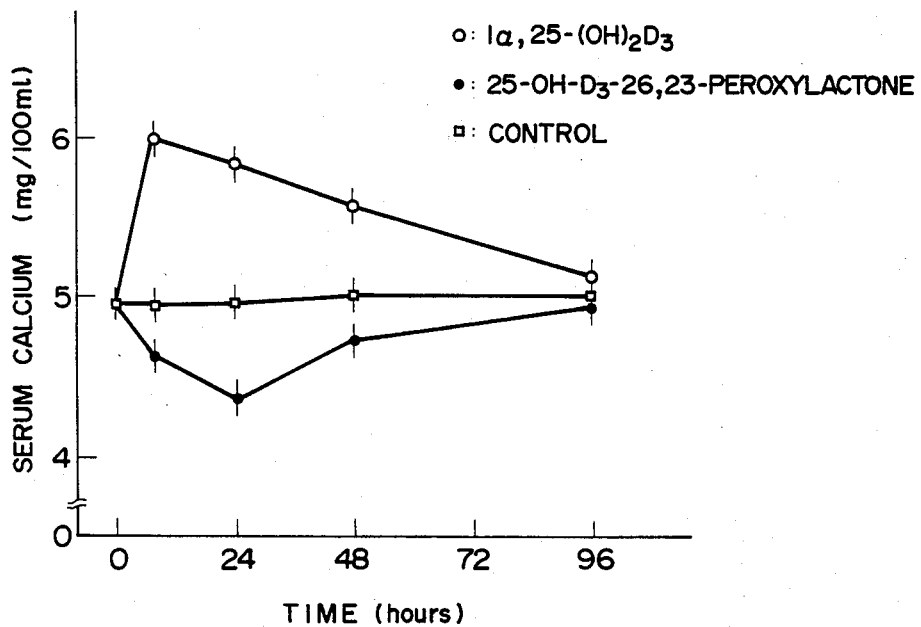

FIG. 2, FIG. 4, and FIG. 6 show that 25-hydroxyvitamin $D_3$-26,23-lactones of the present invention decrease the calcium levels in the serum.

(ii) Dose response relationship between 25-OH-$D_3$-26,23-lactones and intestinal calcium transport and serum calcium levels (a) After 6 weeks on the vitamin D-deficient low calcium diet, rats were divided into groups of 3 or 5 and each rat received a single intravenous dose of 25-OH-$D_3$-26,23-lactone dissolved in 0.2 ml of 0.2% Triton X-100 solution. Control rats received only vehicles. Eight or twenty-four hours later, the animals were decapitated and the intestinal calcium transport and serum calcium concentration were measured as described in the foregoing (i), (a). The results are shown in Table I. The data are expressed as mean±S.E.M. Significantly different from control: a;$p<0.05$, b;$p<0.01$, and c;$p<0.001$.

TABLE I

| Compound | Dose (ng) | Time (hr) | Intestinal Ca transport $^{45}$Ca serosal/ $^{45}$Ca mucosal | Serum Ca (mg/100 ml) |
|---|---|---|---|---|
| Vehicle | | 8 | 1.74 ± 0.16 | 4.74 ± 0.17 |
| 1α,25-$(OH)_2D_3$ | 10 | 8 | 2.48 ± 0.15$^a$ | 4.95 ± 0.18$^a$ |
| | 50 | 8 | 4.20 ± 0.22$^c$ | 5.60 ± 0.18$^c$ |
| | 100 | 8 | 5.06 ± 0.31$^c$ | 5.92 ± 0.20$^c$ |
| | 250 | 8 | 5.33 ± 0.28$^c$ | 6.09 ± 0.22$^c$ |
| 25-OH—$D_3$—26,23-lactone | 100 | 24 | 2.14 ± 0.13$^a$ | 4.80 ± 0.16 |
| | 500 | 24 | 2.65 ± 0.20$^b$ | 4.70 ± 0.18 |
| | 2500 | 24 | 3.27 ± 0.24$^b$ | 4.62 ± 0.21 |

(b) The same experiment as the preceding (a) was conducted with the use of 1α,25-dihydroxyvitamin $D_3$-26,23-lactone. The results are shown in Table II. The data are expressed as mean±S.E.M. Significantly different from control: a;$p<0.05$, b;$p<0.01$, and c;$p<0.001$.

TABLE II

| Compound | Dose (ng) | Time (hr) | Intestinal Ca transport $^{45}$Ca serosal/ $^{45}$Ca mucosal | Serum Ca (mg/100 ml) |
|---|---|---|---|---|
| Vehicle | | 8 | 1.71 ± 0.14 | 4.80 ± 0.10 |
| 1α,25-$(OH)_2D_3$ | 10 | 8 | 2.50 ± 0.15$^a$ | 4.98 ± 0.09$^a$ |
| | 50 | 8 | 4.15 ± 0.20$^c$ | 5.53 ± 0.12$^c$ |
| | 100 | 8 | 5.17 ± 0.18$^c$ | 5.66 ± 0.18$^c$ |
| | 250 | 8 | 5.37 ± 0.23$^c$ | 6.14 ± 0.24$^c$ |
| 1α,25-$(OH)_2D_3$—26,23-lactone | 100 | 8 | 2.26 ± 0.29$^a$ | 4.51 ± 0.16$^a$ |
| | 250 | 8 | 2.70 ± 0.14$^b$ | 4.47 ± 0.12$^b$ |
| | 500 | 8 | 3.13 ± 0.24$^b$ | 4.23 ± 0.13$^c$ |
| | 100 | 24 | 1.96 ± 0.27 | 4.25 ± 0.20$^c$ |
| | 250 | 24 | 2.12 ± 0.22$^a$ | 4.10 ± 0.19$^c$ |
| | 500 | 24 | 2.31 ± 0.20$^a$ | 3.97 ± 0.21$^c$ |

Table I and Table II make it clear that as the dose of 25-hidroxyvitamin $D_3$-26,23-lactones of this invention is stimulated the intestinal clacium transport, the calcium level in the serum is decreased.

(iii) Influence of 25-hydroxyvitamin $D_3$-26,23-lactones on 1α,25-dihydroxyvitamin $D_3$ (a) Rats fed a low calcium vitamin D deficient diet were divided into 4 groups of 5 rats. They received the first dose of 500 ng of 25-OH-$D_3$-26,23-lactone dissolved in 0.2 ml of 0.2% Triton X-100 solution or only vehicle intravenously. Eighty hours later, they received the second dose of 250 ng of 1α,25-$(OH)_2D_3$ dissolved in 0.2 ml of 0.2% Triton X-100 solution or only vehicle by the same route. Fifteen hours after the second dose, the animals were killed and the intestinal calcium transport activity and the serum calcium concentration were measured in the same way as the foregoing (i), (a). The results are shown in Table III. The data are expressed as the mean±S.E.M. Significantly different from control: a;p<0.001.

TABLE III

| Compound | | Intestinal Ca transport $^{45}$Ca serosal/ | Serum Ca |
|---|---|---|---|
| First dose | Second dose | $^{45}$Ca mucosal | (mg/100 ml) |
| Vehicle | Vehicle | 1.71 ± 0.13 | 4.84 ± 0.18 |
| 25-OH—D$_3$—26,23-lactone | Vehicle | 1.80 ± 0.09 | 4.14 ± 0.19$^a$ |
| Vehicle | 1α,25-(OH)$_2$D$_3$ | 3.96 ± 0.18$^a$ | 5.82 ± 0.16$^a$ |
| 25-OH—D$_3$—26,23-lactone | 1α,25-(OH)$_2$D$_3$ | 3.91 ± 0.10$^a$ | 4.88 ± 0.20 |

(b) Rats fed a low calcium vitamin D deficient diet for 6 weeks were divided into 4 groups of 5 rats. They received the first dose of 125 ng of 1α,25-(OH)$_2$D$_3$-26,23-lactone dissolved in 0.2 ml of 0.2% Triton X-100 solution or only vehicle intravenously. Twelve hours later, they received the second dose of 125 nm of 1α,25-(OH)$_2$D$_3$ dissolved in 0.2 ml of 0.2% Triton X-100 solution or only vehicle by the same route. Twelve hours after the second dose, the animals were killed and the intestinal calcium transport activity and the serum calcium concentration were measured in the same way as the aforementioned (i), (a). The results are shown in Table IV. The date are expressed as the mean±S.E.M. Significantly different from control: a;p<0.01 and b;p<0.001.

TABLE IV

| Compound | | Intestinal Ca transport $^{45}$Ca serosal/ | Serum Ca |
|---|---|---|---|
| First dose | Second dose | $^{45}$Ca mucosal | (mg/100 ml) |
| Vehicle | Vehicle | 1.66 ± 0.21 | 4.82 ± 0.09 |
| 1α,25-(OH)$_2$D$_3$—26,23-lactone | Vehicle | 1.79 ± 0.13 | 4.12 ± 0.09$^b$ |
| Vehicle | 1α,25-(OH)$_2$D$_3$ | 3.53 ± 0.14$^b$ | 5.94 ± 0.12$^b$ |
| 1α,25-(OH)$_2$D$_3$—26,23-lactone | 1α,25-(OH)$_2$D$_3$ | 3.62 ± 0.16$^b$ | 5.52 ± 0.12$^a$ |

It is apparent from Table III and Table IV that 1α,25-dihydroxyvitamin D$_3$ raises the calcium levels in the serum remarkably while contrastingly 25-hydroxyvitamin D$_3$-26,23-lactones of the present invention decrease the serum calcium levels remarkably.

Also it is clear that in case where 25-hydroxyvitamin D$_3$-26,23-lactone is administered (as the first dose) before 1α,25-dihydroxyvitamin D$_3$ is administered (as the second dose), the rise of the calcium levels in the serum due to 1α,25-dihydroxyvitamin D$_3$ is brought under control.

(iv) Increase of urinary calcium excretion by 1α,25-(OH)$_2$D$_3$-26,23-lactone

Male weanling rats of rht Wistar strain were fed a vitamin D deficient low calcium diet for 6 weeks. After the ligation of urethras, each of the five rats received an intravenous injection of 125 ng of 1α,25-(OH)$_2$D$_3$-26,23-lactone dissolved in 0.2 ml of 0.2% Triton X-100 solution or only vehicle. Twenty-four hours later, the rats were killed and urine was collected from their urinary bladders. The cencentration of calcium in the urine was determined by the OCPC (O-cresolphthalein complexone) method. the results are shown in Table V.

TABLE V

| Compound | Serum Ca (mg/100 ml) | Urinary Ca excretion (μg) |
|---|---|---|
| Vehicle | 4.90 ± 0.12 | 51.2 ± 3.6 |
| 1α,25-(OH)$_2$D$_3$—26,23-lactone | 3.97 ± 0.07$^b$ | 69.8 ± 4.8$^a$ |

The data are expressed as mean±S.E.M. Significantly different from control: a;p<0.05 and b;p<0.001.

It is clear from Table V that 1α,25-(OH)$_2$D$_3$-26,23-lactone of the present invention enhances the urinary calcium excretion.

EXAMPLE 2

Preparation of elastic capsules

1α,25-dihydroxyvitamin D$_3$-26,23-lactone was dissolved in fatty oil to obtain an oil solution of 7 μg/ml concentration. The shell components consisting of 100 parts by weight of gelatin, 20 parts by weight of glycerin, 0.2 part by weight of ethyl parahydroxybenzoate, 0.2 part by weight of propyl parahydroxybenzoate, 0.5 part by weight of 1-parasulfonylazo-2-naphthol-6-sulfonic acid disodium salt, and 80 parts by weight of purified water were melted by heating to prepare a shell making material. Elastic capsules, each containing 1 μg of 1α,25-dihydroxyvitamin D$_3$-26,23-lactone, were made with the use of thus prepared shell making material on a continuous elastic capsule making machine.

What we claim is:

1. A method to decrease the concentration of calcium in the serum of warm-blooded animals characterized by the administration of a pharmaceutically effective amount of 25-hydroxyvitamin D$_3$-26,23-lactones expressed by the following formula (I) to warm-blooded animals

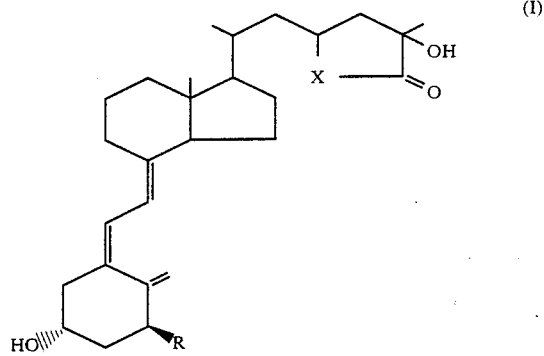

(I)

wherein R indicates a hydrogen atom or a hydroxyl group and X indicates —O— or —O—O—.

2. A method according to claim 1, wherein said 25-hydroxyvitamin D$_3$-26,23-lactones is 1α,25-dihydroxyvitamin D$_3$-26,23-lactone.

3. A method according to claim 1, wherein said pharmaceutically effective amount is 5 ng to 200 ng/kg—body weight/day.

4. A method according to any of claims 1, 2 or 3, wherein said warm-blooded animal is man.

5. A method according to claim 2, wherein said 25-hydroxyvitamin D$_3$-26,23-lactones is 23(S), 25(R)—1α,25-dihydroxyvitamin D$_3$-26,23-lactone.

6. A method according to claim 2, wherein said pharmaceutically effective amount is 5 ng to 200 ng/kg—body weight/day.

7. A method according to claim 5, wherein said pharmaceutically effective amount is 5 ng to 200 ng/kg—body weight/day.

* * * * *